(12) United States Patent
Lee, Jr. et al.

(10) Patent No.: US 7,736,357 B2
(45) Date of Patent: Jun. 15, 2010

(54) RADIOFREQUENCY ABLATION WITH INDEPENDENTLY CONTROLLABLE GROUND PAD CONDUCTORS

(75) Inventors: Fred T. Lee, Jr., Madison, WI (US); Thomas Charles Winter, III, Fitchburg, WI (US); Dieter Georg Haemmerich, Vienna (AT); Lisa Ann Sampson, Cambria, WI (US); S. Nahum Goldberg, Brookline, MA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 811 days.

(21) Appl. No.: 11/214,398

(22) Filed: Aug. 29, 2005

(65) Prior Publication Data

US 2007/0049919 A1 Mar. 1, 2007

Related U.S. Application Data

(63) Continuation of application No. PCT/US05/16172, filed on May 9, 2005.

(60) Provisional application No. 60/569,896, filed on May 11, 2004.

(51) Int. Cl.
*A61B 18/18* (2006.01)
(52) U.S. Cl. .............................. 606/34; 606/32; 606/35
(58) Field of Classification Search ............ 606/34–35, 606/41–42, 32
See application file for complete search history.

(56) References Cited

U.S. PATENT DOCUMENTS

| | | | |
|---|---|---|---|
| 3,720,209 A | 3/1973 | Bolduc | |
| 3,960,141 A | 6/1976 | Bolduc | |
| 4,799,480 A | 1/1989 | Abraham et al. | |
| 5,196,008 A * | 3/1993 | Kuenecke et al. | 606/35 |
| 6,350,276 B1 | 2/2002 | Knowlton | |
| 6,544,258 B2 * | 4/2003 | Fleenor et al. | 606/32 |
| 6,740,080 B2 * | 5/2004 | Jain et al. | 606/34 |
| 6,860,881 B2 * | 3/2005 | Sturm et al. | 606/35 |
| 7,137,980 B2 * | 11/2006 | Buysse et al. | 606/34 |
| 2002/0022864 A1 | 2/2002 | Mahvi et al. | |
| 2002/0120304 A1 | 8/2002 | Mest | |
| 2002/0128640 A1 | 9/2002 | Swanson | |
| 2002/0156472 A1 | 10/2002 | Lee et al. | |
| 2003/0028183 A1 | 2/2003 | Sanchez et al. | |
| 2003/0093007 A1 | 5/2003 | Wood | |
| 2003/0158548 A1 | 8/2003 | Phan et al. | |
| 2004/0230187 A1 | 11/2004 | Lee et al. | |
| 2005/0010209 A1 | 1/2005 | Lee, Jr. et al. | |
| 2005/0080409 A1 * | 4/2005 | Young et al. | 606/41 |

FOREIGN PATENT DOCUMENTS

| | | |
|---|---|---|
| GB | 1333573 | 10/1973 |
| WO | WO 96/34571 | 11/1996 |
| WO | WO 03/047446 | 6/2003 |

* cited by examiner

*Primary Examiner*—Lee S Cohen
(74) *Attorney, Agent, or Firm*—Boyle Fredrickson, S.C.

(57) ABSTRACT

A radiofrequency ablation system provides multiple ground pads and active control of current flow through the ground pads to provide improved power sharing at the tissue near the ground pads reducing risk of patient skin burns for higher power ablation generators.

19 Claims, 5 Drawing Sheets

FIG. 1
PRIOR ART
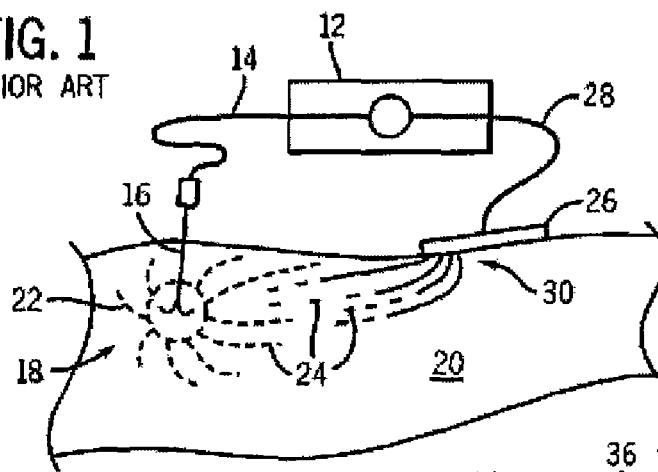
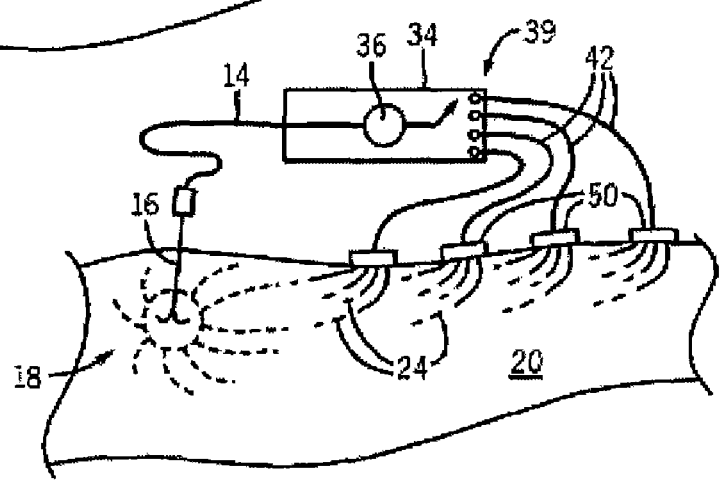
FIG. 2
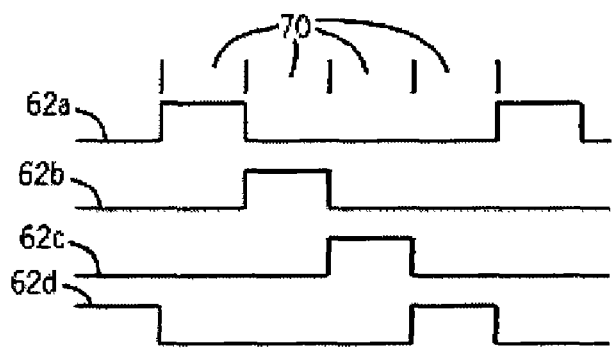
FIG. 3
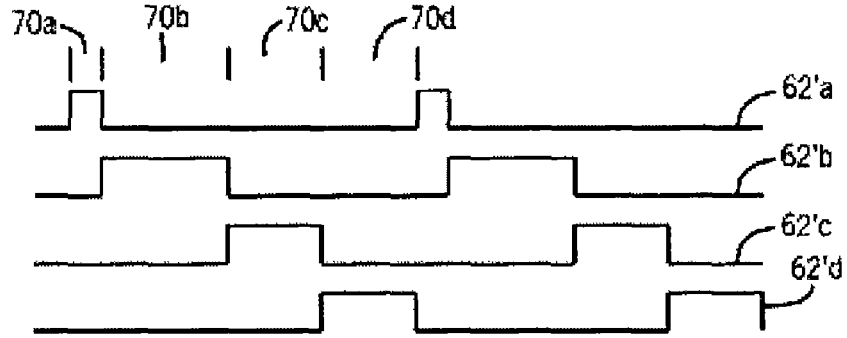
FIG. 5

RADIOFREQUENCY ABLATION WITH INDEPENDENTLY CONTROLLABLE GROUND PAD CONDUCTORS

CROSS-REFERENCE TO RELATED APPLICATIONS

This application is a continuation of PCT Application Ser. No. US05/16172 filed May 9, 2005 entitled "Radiofrequency Ablation with Independently Controllable Ground Pad Conductors" which claims the benefit of U.S. Provisional application 60/569,896 filed May 11, 2004.

STATEMENT REGARDING FEDERALLY SPONSORED RESEARCH OR DEVELOPMENT

This invention was made with United States government support awarded by the following agencies: NIH DK058839. The United States has certain rights in this invention.

BACKGROUND OF THE INVENTION

The present invention relates to radio frequency ablation of tumors and the like, and in particular to a method using multiple ground pads, or multiple independent ground pad elements within a single pad, to reduce the risk of skin burns.

Ablation of tumors, such as liver (hepatic) tumors, uses heat or cold to kill tumor cells. In radiofrequency ablation (RFA), an electrode is inserted into the tumor and current passing from the electrode through the patient to a large area "dispersive" or ground pad on the patient's skin destroys the tumor cells through resistive heating. At the electrode, the current density is high as a result of the relatively small interface area of the electrode. This results in high rates of energy deposition, through resistive heating, creating high temperatures sufficient for ablation. Conversely, and ideally, the current density at the ground pad is low as a result of the large interface area of the ground pad, resulting in lower temperatures easily tolerated by the skin and intervening tissues.

The desire for improved ablation and ablation of larger tumors has prompted a move toward ablation power supplies with greater power. This increased power has increased current densities at the ground pad increasing the risk of patient skin burns. Attempts have been made to compensate for high electrical power by using multiple ground pads connected in series or parallel. Multiple ground pads provide a greater ground pad area decreasing current density and power deposition at the skin. This approach, however, has not always been satisfactory in reducing burns. Further, when multiple ground pads are used, they must be carefully adjusted to be approximately equal resistive distance from the ablation site to share properly the return current.

BRIEF SUMMARY OF THE INVENTION

One reason multiple ground pads may be ineffective is that current concentrates at the leading edge (i.e. the edge closest to the ablation electrode) of the ground pad toward the ablation electrode. The concentration of current reduces the effectiveness of the area behind the leading edge. Further, it may be difficult in practice to properly locate multiple ground pads to promote sharing of current among the ground pads. Accordingly, the present invention actively controls current flow through multiple ground pads independent of the relative resistance between the ground pads and the ablation electrode.

Most simply, this control of current is done by switching between different ground pads. In this way, sharing of the power dissipation is enforced despite resistive differences. The switching may be according to a predetermined fixed schedule, or may be controlled using temperature or impedance feedback ensuring the best utilization of each ground pad. Continuous current control without switching may also be used.

Specifically, the present invention provides a radiofrequency ablation system having at least one ablation electrode for insertion into a patient at an ablation site and at least two ground pads (or at least two independent elements within a single pad) for topical application to a portion of the patient's skin. A power supply independently applies a radiofrequency voltage between the ablation electrode and the ground pads to ablate tissue at the ablation site.

Thus, it is one object of an embodiment of the invention to actively control power flowing in a path through a ground pad so as to enforce a proper sharing of power between ground pads reducing the opportunity for patient burns.

The power supply may switch the application of voltage first between an ablation electrode and a first ground pad, and second between the ablation electrode and a second ground pad.

Thus, it is another object of at least one embodiment of the invention to provide a simple method of independently applying power between an ablation electrode and multiple ground pads.

The switching may be according to a predetermined fixed time schedule.

Thus, it is an object of one embodiment of the invention to provide a simple method of sharing between ground pads that does not require monitoring ground pad current or temperature.

Alternatively, the ground pad electrodes may include temperature sensors and the power supply may apply the voltage independently between the ablation electrode and ground pads as a function of the temperature at the ground pad.

Alternatively, the impedance between the electrode and each ground pad may be measured (or parameters related to impedance such as current flow) and used to control the voltage according to this impedance.

Thus, it is another object of at least one embodiment of the invention to provide sophisticated control of power sharing between ground pads that may accommodate differences in the locations of the ground pads, their electrical connection to the skin, the ability of skin region tissue to dissipate heat, and the relative resistance between the ablation electrode and each ground pad.

The power supply may limit power dissipated between each of the ablation electrodes and ground pads to a predetermined value.

It is thus another object of at least one embodiment of the invention to allow relative freedom in the location of multiple ground pads without promoting excess current flow between the ablation probe and one ground pad.

The ground pad may provide mutually insulated conductive areas.

Thus it is another object of at least one embodiment of the invention to provide an easily applied ground pad that provides independently controllable conductive zones.

The ground pad may be actively cooled, for example, by passing a cool fluid over the top of the ground pad or the like.

It is thus another object of at least one embodiment of the invention to provide a method of reducing the risk of skin burns that may be combined with other cooling techniques.

A power supply for use with this system may include a ground pad verification circuit providing a signal indicating the number of ground pads connected to the power supply to control the power based on that signal.

Thus it is another object of at least one embodiment of the invention to provide a system that intelligently determines whether sufficient ground pad capability exists.

The system may respond to the number of ground pads by reducing the maximum power output by the power supply, and possibly further limiting the type or number of ablation electrodes that can be used according to the reduced power output.

Thus it is another object of at least one embodiment of the invention to provide a system that may be flexibly used at different power settings either with single ground pads, multiple jointly controlled ground pads, or multiple independently controlled ground pads.

These particular objects and advantages may apply to only some embodiments falling within the claims and thus do not define the scope of the invention.

BRIEF DESCRIPTION OF THE DRAWINGS

FIG. 1 is a simplified view of a conventional ablation system in which current flows from an ablation probe at an ablation area to a ground pad showing concentration of current flow at the leading edge of the ground pad;

FIG. 2 is a figure similar to that of FIG. 1 showing the use of multiple switched ground pads to distribute the area of current concentration among multiple ground pads;

FIG. 3 is a timing diagram of the application of power to the multiple ground pads of FIG. 2 in a simple fixed schedule system;

FIG. 5 is a timing diagram similar to that of FIG. 3 showing adjustment of the duty cycle of power flow at a particular ground pad as a function of temperature or impedance measured at that ground pad;

DETAILED DESCRIPTION OF THE PREFERRED EMBODIMENT

Figure 4:
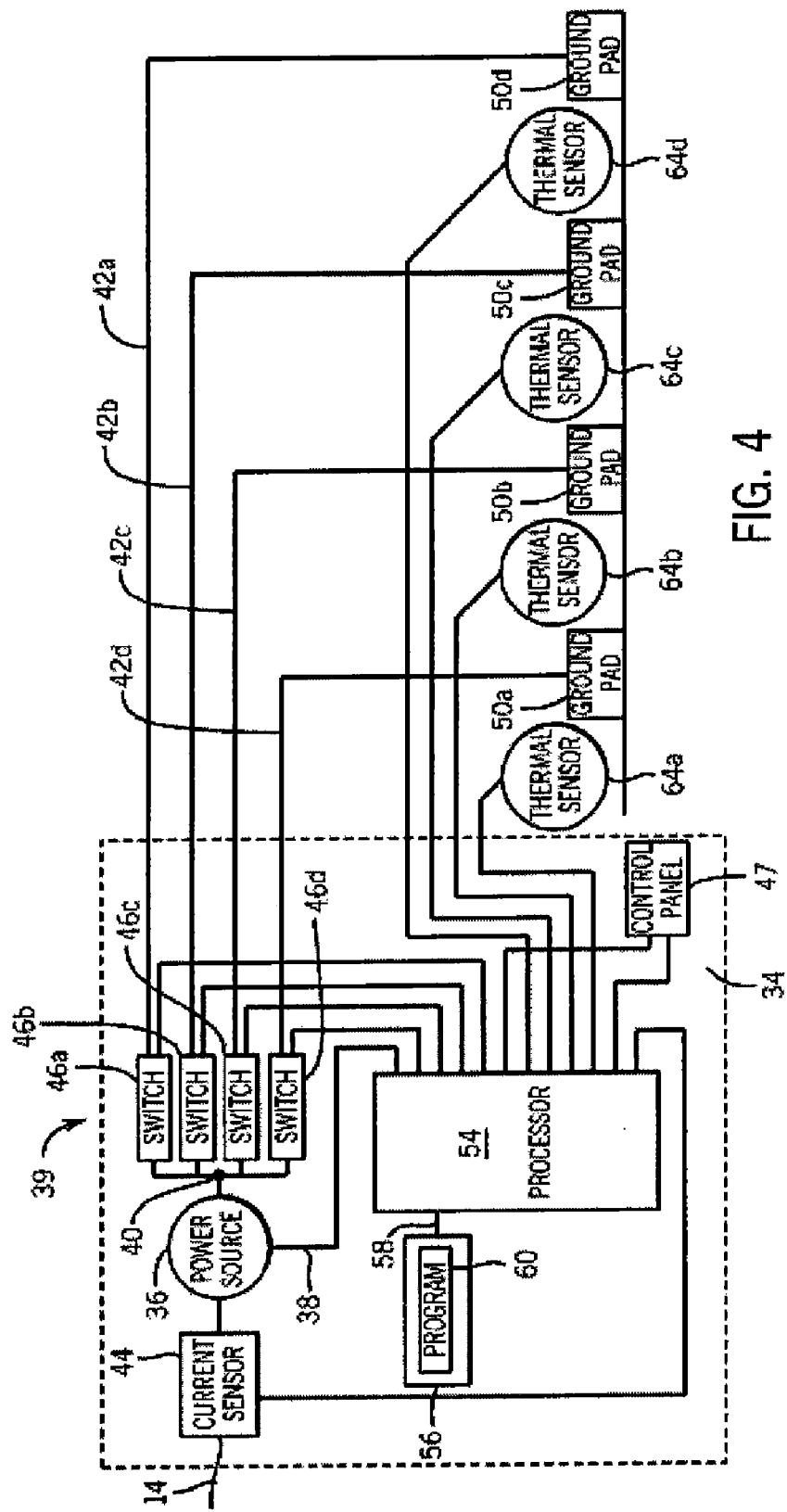
FIG. 4 is a detailed fragmentary view of a microprocessor controlled power supply providing switching among ground pads according to an impedance and/or temperature monitoring.

Referring now to FIG. 1 in a prior art ablation system, a radiofrequency power supply 12 provides a first terminal connected to an ablation lead 14 providing power to an ablation electrode 16. The ablation electrode 16 has an active end 18 inserted within a patient 20 to an ablation site 22 typically being the location of a tumor or the like.

Electrical power may flow from the power supply 12 to the end 18 where resistive heating caused by current 24 causes a destruction of tumor cells. The current 24 disperses through the body of the patient 20 to return to a ground pad 26 having a broad contact area on the patient's skin. The ground pad 26 is provided with a lead 28 returning to the power supply 12 to complete the electrical circuit.

While the present inventors do not wish to be bound by a particular theory, it is believed that electrical current 24 concentrates at the leading edge of the ground pad 26 producing a hot spot 30 that may create a risk of patient burns. This concentration of current 24 results from the fact that the leading edge is closest to the end 18 of the ablation electrode 16 and thus provides a path of least electrical resistance.

Referring now to FIG. 2, a power supply 32 per the present invention includes a power source 36 also providing alternating radiofrequency power to an ablation lead 14 providing power to an ablation electrode 16 with an end 18 inserted within a patient 20 at an ablation site 22. In this case, however, the current 24 returns to multiple ground pads 50 having multiple areas of contact with the patient's skin. The power supply 32 includes a switch system 39 alternately connecting the power source 36 to one of the ground pads 50 via separate conductors 42.

Referring now to FIG. 4, one terminal of the power source 36 connects to ablation lead 14 through a current sensor 44 while the other terminal connects to a branch point 40 leading to a set of conductors 42a-42b. The conductors 42a-42b pass through solid state switches 46a through 46d to connect to electrically independent ground pads 50a through 50d. Each of the ground pads 50a through 50d includes a thermal sensor 64a through 64b.

The power supply 34 includes a processor 54 communicating with a memory 56 via an internal bus 58. The processor 54 provides a set of input lines receiving analog voltages from each of the thermal sensors 64a through 64d and from the current sensor 44 to be converted into digital values by an internal analog to digital converter. The processor also receives an analog value of the voltage provided by power supply 34, via line 38 enabling computation of the impedance. Further the processor 54 provides a series of binary output lines passing to and controlling each of the solid state switches 46a through 46d and an analog control line 38 providing a signal to the power source 36 controlling the voltage and/or current produced by the power source 36. The processor 54 also provides input and output lines to front panel controls as will be described below.

Referring now to FIGS. 2 and 3, in a first embodiment, the processor 54 may sequentially activate switches 46 to provide waveforms 62a through 62d as control signals for switches 46a through 46d, so that current flows through conductors 42a through 42d during the corresponding on-times of these waveforms. These waveforms 62a through 62d switch the flow of ablation current 24 between the end 18 of the ablation electrode 16 and one ground pad 50a through 50d at a time, rotating through each of the particular ground pads 50a through 50d before returning again to repeat this rotation. As shown in FIG. 3, the current flow on-time 70 on each of the conductors 42a through 42d may, in the first case, be equal dividing the total ablation-time, power and current by the number of ground pads 50a through 50d, in this example, four. Note, that this switching between ground pads 50a through 50d nevertheless provides continuous or near continuous current flow at the ablation electrode 16 and thus, while the electrical power dissipated at each ground pad 50a through 50d is reduced by one-fourth, the electrical power dissipated at the ablation site 22 is not reduced. The voltage output from the power source 36 may be controlled alternatively or in addition.

As shown in FIG. 2, at each ground pad 50a through 50d, some concentration of current will occur at the leading edge. Nevertheless, the result of the switching of FIG. 3 is that the total heating of the leading edge of each ground pad 50a through 50d is reduced by one-fourth or more generally by the number of different independently controlled ground pads 50. Further, sharing of current between the ground pads 50a through 50d (across time) is forced by the activation of only one ground pad 50a through 50d at a time. The switching speed and thus the absolute duration of the on-times 70 may be adjusted to a high rate so that the tissue near the ground pads 50 practically experiences a continuous heat load.

Referring now to FIG. 4, generally a single ground pad 50a, for example, may be closer to the ablation site 22 or there may be other local variation in the site of the ground pad 50a, for example, the presence or absence of large heat dissipating blood vessels or differences in the contact resistance between the ground pad 50a and the patient 20, that affect equal sharing of power among the ground pads 50a through 50d. Accordingly, in a second embodiment, the thermocouples 64a through 64d or other similar temperature measuring component associated with each of the ground pads 50a through 50d, may provide signals used by the processor 54 to further control the power to each of the ground pads 50a through 50d.

The switching between different ground pads 50 should not produce significant stimulation of excitable tissues like nerves, muscle, and heart which can be excited by low frequency signals typically below approximately 100 kHz. To avoid excitation, the switching may be done at frequencies above the frequency threshold for excitation. Alternatively, the switching can be limited to zero crossings of the RF signal delivered by the generator, or high pass filters with corner frequencies approximately 100 kHz can be placed in parallel to the generator to remove low frequency components.

As shown in FIG. 5, the processor 54 may generate waveforms 62a through 62d in which total on-times 70a through 70d may be adjusted. For example, waveforms 62a may have an on-time 70a less than the on-times 70b, 70c and 70d of waveforms 62b through 62d to limit power to the ground pad 50 caused by relatively higher temperatures at ground pad 50a. Generally, the processor 54 may execute a closed loop feedback control using well-known control techniques such as PID loops to endeavor to equalize the temperatures at each of the ground pads.

Referring still to FIGS. 4 and 5, alternatively, the on-times 70a through 70d may be controlled as a function of the measured impedance during each of the on-times 70a through 70d as determined by current sensors 44 and knowledge of the voltage amplitude of the power source 36 from voltage sensing line 39. This impedance, providing an indication of possible tissue heating in the vicinity of the ground pads 50a through 50d may be simply calculated from knowledge of the voltage produced by the power source 36 divided by the current flow during the activation of each ground pad 50. The impedance may alternatively be used in addition to temperature measurement to change the on-times 70a through 70d. Generally an on-time 70 is decreased as temperature or impedance rises.

Figure 11:
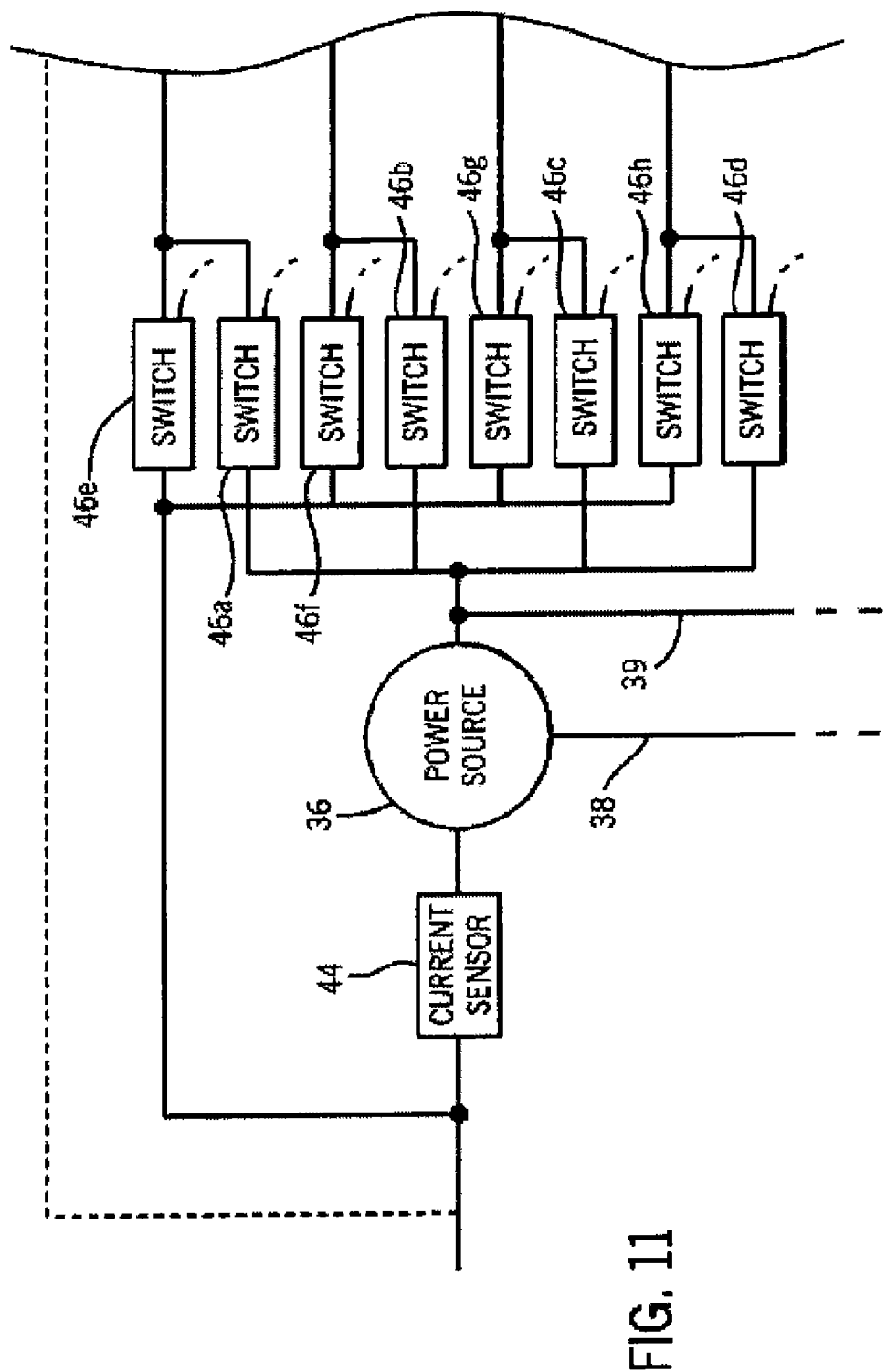
FIG. 11 is a fragmentary view of FIG. 4 showing an alternative circuit for measuring impedance between ground pads.

Alternatively, impedance could be measured between any pair of ground pads 50a through 50d, and serve as means for adjusting on-time or identifying bad ground connections. This impedance measurement can be done by use of a separate impedance measuring circuit or as shown in FIG. 11, by adding a second set of switches 46e-46h to the power supply 36 to allow low power to be applied (for example, before or periodically during the ablation) between any two of the pads 50 and the impedance measured using the current sensor 44 and voltage line 39.

This measurement would provide a more accurate value of electrical connection of each ground pad because generally only tissue right below the pads 50 contributes to the impedance. Generally, under the control of the processor 54, the impedance between each pair of pads 50 may be measured. If the impedance between pads 50a and 50b, for example, is much higher than the impedance between pads 50b and 50c, it can be deduced that the pad 50a is the ground pad with a bad connection and so forth. Multiple high impedance connections may be isolated with a more sophisticated analyses of this information as will be understood to those of ordinary skill in the art. As well as adjusting the on-times, this information can be provided to the user through a display or the like.

This impedance measurement may also be used to ascertain the presence of multiple ground pads 50a through 50d as will be described below prior to the initiation of the ablation.

The processor 54 executing the stored program 60 may further limit the absolute power provided on any of the conductors 42a through 42d by controlling the voltage of the power source 36 in response to instantaneous current measurements from the current sensor 44. This power limitation provides some protection against the possibility of a thermal sensor 64 or ground pads 50 being missing or disconnected. This power limitation also provides a simple level of control of power to each of the ground pads 50a through 50d in addition to or in lieu of the switching described above. It will be understood, however, that the simple multiplexing arrangement described with respect to FIG. 3 affects a natural reduction in power in the event of ground pad failure.

The independent control of power to each of ground pads 50a through 50d allows greater flexibility in locating the ground pads eliminating the need to carefully balance them so that their resistive paths to the ablation electrode 16 are the same or nearly the same.

Figure 6:
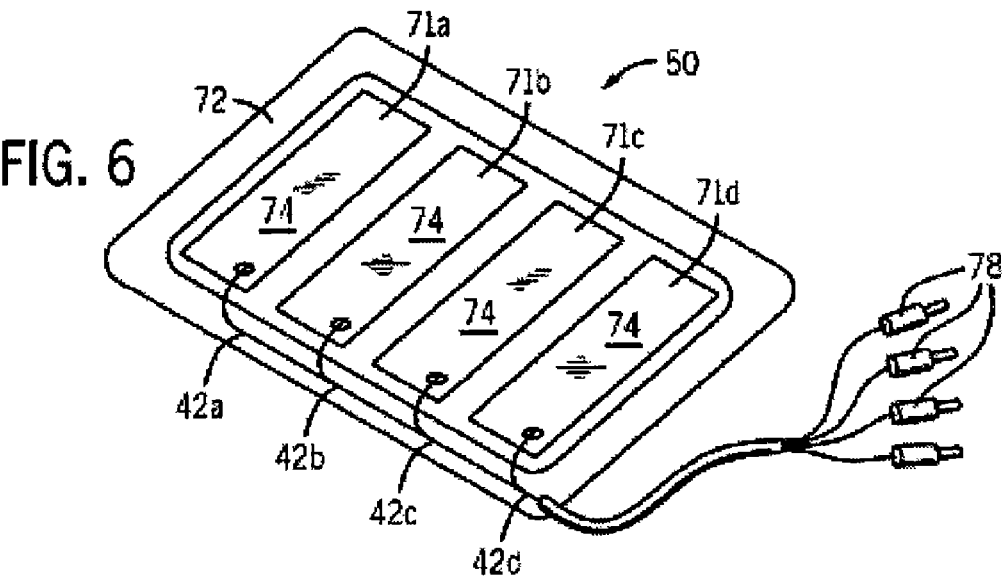
FIG. 6 is a perspective view of the skin side of a multiple conductor ground pad such as may be used with the present invention.

Referring now to FIG. 6, the effect of concentration of power dissipation at the leading edge of a ground pad 50 means that a ground pad 50 of a given area can provide improved performance if it is broken into multiple conductive regions 71a through 71d having the same total area or different areas. Each of these regions 71a through 71d may act like independent ground pads 50 and be attached to a common support pad 72 having an adhesive 74 on its skin side for easy placement against the patient 20. Typically, a gel with conductive properties will be placed on the conductive region 71a or a gel will be applied at the time of application.

Each of the regions 71a through 71d may have a separate conductor 42a through 42d terminating in a connector 78 that may be attached to the power supply 32 for independent control of the current flow into region 71a through 71d and may be associated with a thermocouple 64 (not shown). Here the regions 71a through 71d operate effectively as separate ground pads 50.

Figure 7:
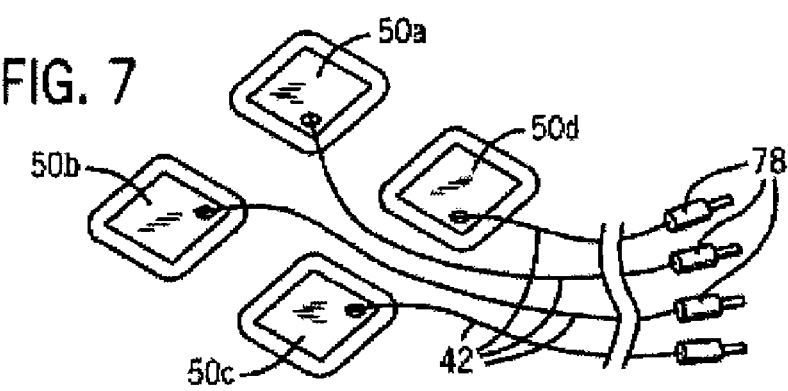
FIG. 7 is a view of an alternative ground pad arrangement in which multiple standard ground pads are used.

Referring now to FIG. 7, alternatively, conventional, physically separate ground pads 50a through 50c may be used, each providing a separate conductor 42 and separate connector 78.

Figure 8:
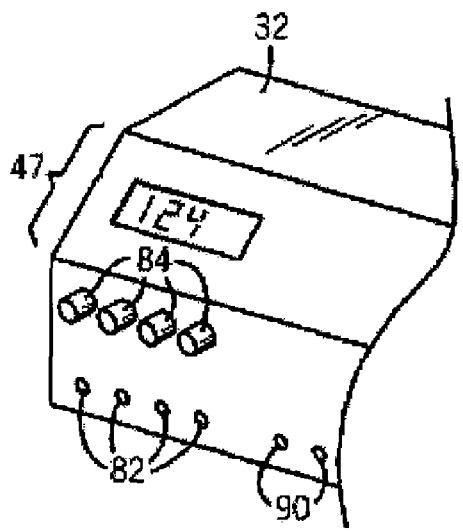
FIG. 8 is a perspective view of power supply providing for multiple ground pad inputs together with user controls controlling the relative power at each ground pad.

Referring now to FIG. 8, the power supply 32 may include a front panel providing for multiple connectors 82 for receiving each of the connectors 78. Control knobs 84 being part of a control panel 47 communicating with the processor 54 may be associated with each of the connectors 82 allowing information about power dissipation through the associated ground pad 50 to be read from a readout 86 and for manual control of current sharing between those ground pads 50 when that is desired. The setting provided by the knobs 84 may modify the on-times 70 by applying an additional factor to the on-time calculation (for example, by changing one of the PID parameters) or may change a maximum power for the particular ground pad 50.

Additional connectors 90 provide for the use of multiple ablation electrodes 16 as may be desired in certain instances.

Figure 9:
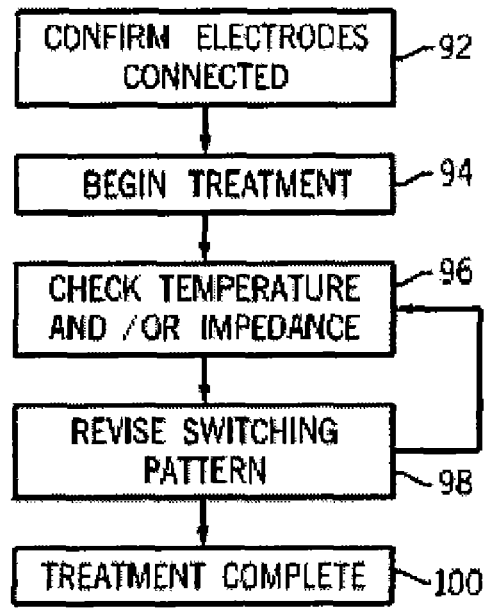
FIG. 9 is a flow chart of firmware executed in the processor of FIG. 4 during a typical ablation procedure.

Referring now to FIG. 9, in use the processor 54 of the power supply 32 executes the stored program 60 to optionally confirm the presence of multiple ground pads 50 as indicated by process block 92. The confirmation may make use of measurements of impedance between the ablation electrode 16 and each of the ground pads 50 at low power or may measure impedance between a given ground pad and other ground pads 50 to ensure that they are all communicating with the patient. Alternatively, a mechanical confirmation may be provided by detection of insertion of the connectors 78 into connectors 82 which may incorporate switches of a type well known in the art.

As noted above, a single missing ground pad 50 will generally not upset the sharing of power dissipation among the remaining ground pads 50, but may affect the maximum power than can be handled. Accordingly, indication of a missing ground pad may be used to limit the maximum power provided by the power source 36.

As indicated by process block 94, the ablation treatment may then begin using a predetermined schedule as shown in FIG. 3. The schedule may control on-times 70 and/or voltage output from the power source 36

At process block 96, temperature and/or impedance may be measured and used to adjust the schedule of FIG. 3 as indicated by process block 98. This process of process block 94, 96, and 98 may continue until ablation is completed as indicated by process block 100. At this process block, the output power may also be calculated (voltage times current) for each ground pad 50*a* through 50*d* and the voltage of the power source 36 for each of the ground pads 50*a* through 50*d* adjusted.

While switching of the connections of the ground pads 50*a* through 50*d* is shown, it will be understood that in an alternative embodiment, solid state current control elements may be used instead of switches 46 to provide continuously variable control, the current flow allowing simultaneous energizing of the ground pads 50*a* through 50*d*. This is not the preferred embodiment, however, because there may be some current shielding effects when multiple ground pads 50*a* through 50*d* are simultaneously energized.

Figure 10:
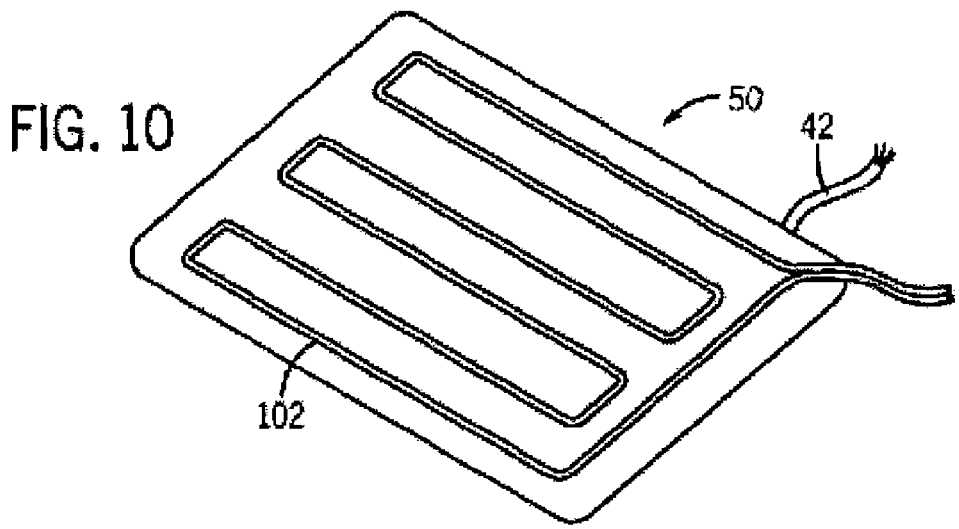
FIG. 10 is a view of a backside of the electrode of FIG. 6 having provision for active cooling of the ground pad and thus the skin region near the ground pad.

Referring now to FIG. 10, the present invention significantly reduces the heat dissipated on the skin in the vicinity of a given ground pad 50. However, this invention may be used with auxiliary techniques to improve the amount of power that can be safely extracted from the tissue of the patient. For example, a second side of the ground pad 50 away from the patient may include a serpentine hose 102 through which chilled gas or liquid may be passed so as to cool the ground pad 50 and by conduction the tissue in the vicinity of the ground pad 50, thus reducing the possibility of patient burns or discomfort. Cooling may be controlled by the thermal sensor elements or may be operated open-loop to provide an additional method of reducing heating of this skin tissue.

It will be understood that the present invention is not limited to any particular number of ground pads 50 but may make use of an arbitrarily large number of ground pads 50 with improved dissipation effects being realized with increased numbers of ground pads 50. The ground pads 50 may be advantageously shaped to increase their leading edge area with respect to their total area.

While the present invention contemplates that the switching or other control of the current in the ground pads 50 occurs within the housing of the power supply 32, it will be understood that some switching elements may be placed directly at the ground pads 50 to provide for simplified cabling in which power is introduced to the ground pads 50, for example, in parallel through a daisy chain connection system and switched locally by signals contained over other conductors or wirelessly or by carrier current for other technique.

It is specifically intended that the present invention not be limited to the embodiments and illustrations contained herein, but include modified forms of those embodiments including portions of the embodiments and combinations of elements of different embodiments as come within the scope of the following claims.

We claim:

1. A radio frequency ablation system comprising:
    at least one ablation electrode for insertion into a patient at an ablation site;
    at least two ground pad conductors for topical application to a portion of the patient's skin; and
    a power supply independently applying a radio frequency voltage between the at least one ablation electrode and the at least two ground pad conductors to ablate tissue at the ablation site;
    wherein the power supply switches an application of the voltage first between the at least one ablation electrode and a first ground pad conductor, and second between the at least one ablation electrode and a second ground pad conductor according to a predetermined time schedule.

2. The radiofrequency ablation system of claim 1 wherein the at least two ground pad conductors include temperature sensors and wherein the power supply applies the voltage independently between the at least one ablation electrode and the at least two ground pad conductors also as a function of temperature at the ground pad conductor.

3. The radiofrequency ablation system of claim 1 wherein the power supply applies the voltage independently between the at least one ablation electrode and the at least two ground pad conductors also as a function of an impedance between the at least one ablation electrode and the at least two ground pad conductors.

4. The radiofrequency ablation system of claim 1 wherein the power supply independently controls the power dissipated between each of the at least one ablation electrode and the at least two ground pad conductors to at least one predetermined value.

5. The radiofrequency ablation system of claim 4 wherein the predetermined value is a constant value.

6. The radiofrequency ablation system of claim 1 wherein the at least two ground pad conductors are different mutually insulated conductive areas of an integral pad unit.

7. The radio frequency ablation system of claim 1 wherein the at least two ground pad conductors are actively cooled.

8. A radiofrequency ablation power supply comprising:
    an electrical connector accepting a mating connector to an ablation electrode for insertion into a patient at an ablation site;
    at least two additional electrical connectors accepting mating connectors for at least two ground pad conductors for topical application to a portion of the patient's skin;
    independent power regulation circuitry controlling the power applied to tissue at the ablation site, wherein the power applied to the tissue at the ablation site is a function of the current passing through a first ground pad conductor and the current passing through a second ground pad conductor;

a clock circuit controlling a switching of the power regulation circuitry according to a predetermined time schedule; and a power source configured for regulation by the independent power regulation circuitry.

9. The radio frequency ablation power supply of claim 8 wherein the power regulation circuitry is electronically controlled switches interposed between the power source and each of the at least two additional electrical connectors for alternating connecting the power source and the two additional electrical connectors.

10. The radiofrequency ablation power supply of claim 8 further including inputs receiving a temperature signal associated with the at least two ground pad conductors and wherein the power regulation circuitry controls the power associated with current through the at least two ground pad conductors as a function of temperature at the at least two ground pad conductors.

11. The radiofrequency ablation power supply of claim 8 wherein the power regulation circuitry controls the power associated with current through each of the at least two ground pad conductors, as a function of impedance between the ablation electrode and the at least two ground pad conductors.

12. The radiofrequency ablation power supply of claim 8 wherein the power regulation circuitry limits the power associated with the at least two ground pad conductors to at least one of predetermined value.

13. The radiofrequency ablation power supply of claim 12 wherein the predetermined value is a constant value.

14. The radiofrequency ablation power supply of claim 8 further including a ground pad verification circuit providing a signal indicating a number of ground pad conductors connected to the power supply to control the power supply based on that signal.

15. The radiofrequency ablation power supply of claim 8 further providing user controls allowing user modification of the power applied to tissue at the ablation site by controlling the current passing through the first ground pad conductor and the power applied to tissue at the ablation site by controlling the current passing through the second ground pad conductor.

16. A method of radiofrequency ablation comprising the steps of:

(a) inserting at least one ablation electrode into a patient at an ablation site;

(b) attaching at least two ground pad conductors in electrical communication with a portion of the patient's skin; and (c) applying a radiofrequency voltage between the ablation electrode and ground pad conductors to ablate tissue at the ablation site while independently adjusting a current flow at each of the ground pad conductors to reduce risk of skin burns;

wherein the radiofrequency voltage is switched according to a fixed periodic schedule from between the at least one ablation electrode and a first ground pad conductor to between the at least one ablation electrode and a second ground pad conductor.

17. The method of radiofrequency ablation of claim 16 further including the step of controlling the current between the ablation electrode and each ground pad conductor as a function of temperature at the ground pad conductor.

18. The method of radiofrequency ablation of claim 16 further including the step of controlling the current between the ablation electrode and each ground pad conductor as a function of impedance between electrode and the ground pad conductors.

19. The method of radiofrequency ablation of claim 16 wherein the power dissipated between the ablation electrode and each of the ground pad conductors is limited to a predetermined value.

* * * * *